United States Patent
Wack et al.

(10) Patent No.: US 6,699,290 B1
(45) Date of Patent: *Mar. 2, 2004

(54) MODULAR ELBOW

(75) Inventors: Michael A. Wack, Warsaw, IN (US); Arnold-Peter C. Weiss, Barrington, RI (US); D. Steven Block, Warsaw, IN (US); Austin W. Mutchler, Warsaw, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/440,014

(22) Filed: Nov. 12, 1999

Related U.S. Application Data

(63) Continuation-in-part of application No. 09/222,601, filed on Dec. 29, 1998, now Pat. No. 6,290,725, which is a continuation-in-part of application No. 08/963,138, filed on Nov. 3, 1997, now Pat. No. 6,027,534.

(51) Int. Cl.$^7$ .................................................. A61F 2/38
(52) U.S. Cl. ................................. 623/20.12; 623/19.13; 623/21.17
(58) Field of Search .......................... 623/20.11, 20.12, 623/20.13, 18.11, 19.13, 21.17, 21.11, 20

(56) References Cited

U.S. PATENT DOCUMENTS

| | | | |
|---|---|---|---|
| 3,708,805 A | 1/1973 | Scales et al. | |
| 3,939,496 A | 2/1976 | Ling et al. | |
| 4,057,858 A | 11/1977 | Helfet | |
| 4,079,469 A | 3/1978 | Wadsworth | |
| 4,106,128 A | 8/1978 | Greenwald et al. | |
| 4,136,405 A | 1/1979 | Pastrick et al. | |

(List continued on next page.)

OTHER PUBLICATIONS

Advertising literature, "All the right pieces for . . . Outstanding Performance," The Kudo Elbow, Biomet Ltd, date unknown.

Two pages of advertising literature for The Capitello-–Condylar Total Elbow, Johnson & Johnson Products, Inc. Orthopaedic Division, date unknown.

"Surgical Technique for the Capitello–Condylar Total Elbow Prosthesis," Frederick C. Ewald, M.D., date unknown.

(List continued on next page.)

Primary Examiner—Paul B. Prebilic
(74) Attorney, Agent, or Firm—Maginot, Moore & Beck

(57) ABSTRACT

A modular elbow prosthesis includes a humeral and ulnar components and three bearing components. The ulnar component includes a stem and a body including a slot. Two of the three bearing components include flanges that mate with the slot of the ulnar component. The humeral component includes a stem and two arms extending from one end of the stem. An opening is formed in each arm and in two of the three bearing components. The modular elbow may be used in an unconstrained mode by attaching one bearing component to the ulnar component and the other to the humeral component by inserting a pin through the openings in the arms and the bearing component. The two bearing components are then placed adjacent each other such that they articulate about their bearing surfaces. Alternatively, the prosthesis can be utilized in a constrained mode by positioning the flange of the third bearing component in the slot on the ulnar component and positioning the third bearing component between the arms of the humeral component and inserting a pin through the openings in the arms of the third component. In another alternative embodiment, one bearing component may surround a portion of the other bearing component. The components may be joined by a pin to form a constrained elbow prosthesis. In one embodiment, two of the bearing surfaces are configured to permit axial rotation without becoming disengaged. In other embodiments, the various components may be held together by a taper lock.

13 Claims, 11 Drawing Sheets

U.S. PATENT DOCUMENTS

| | | |
|---|---|---|
| 4,193,139 A | 3/1980 | Walker |
| 4,224,695 A | 9/1980 | Grundei et al. |
| 4,242,758 A | 1/1981 | Amis et al. |
| 4,261,064 A | 4/1981 | Helfet |
| 4,280,231 A | 7/1981 | Swanson |
| 4,293,963 A | 10/1981 | Gold et al. |
| 4,301,552 A | 11/1981 | London |
| 4,383,337 A * | 5/1983 | Volz et al. ............... 623/20.11 |
| 4,462,120 A | 7/1984 | Rambert et al. |
| 4,538,306 A | 9/1985 | Dorre et al. |
| 4,822,366 A | 4/1989 | Bolesky |
| 4,923,472 A | 5/1990 | Ugolini |
| 4,936,853 A | 6/1990 | Fabian et al. |
| 4,950,298 A | 8/1990 | Gustilo et al. |
| 4,985,037 A | 1/1991 | Petersen |
| 5,030,237 A | 7/1991 | Sorbie et al. |
| 5,194,066 A | 3/1993 | Van Zile |
| 5,330,534 A | 7/1994 | Herrington et al. |
| 5,376,121 A | 12/1994 | Huene et al. |
| 5,507,817 A * | 4/1996 | Craig et al. ................... 623/18 |
| 5,755,804 A | 5/1998 | Schmotzer et al. |
| 5,879,390 A | 3/1999 | Kubein-Meesenburg et al. |
| 6,361,563 B2 * | 3/2002 | Terrill-Grisoni et al. . 623/20.11 |
| 6,379,387 B1 * | 4/2002 | Tornier ................... 623/20.12 |

OTHER PUBLICATIONS

Article entitled "Biomechanics of the Total Elbow Arthroplasty," Patrick M. Connor and Kai–Nan An, Seminars in Arthroplasty, vol. 9, No. 1 (Jan.), 1998, pp. 25–31.

Six pages of leaflet entitled "The Cavendish Elbow," Thackray® Orthopaedic, date unknown.

Two pages of literature concerning nonconstrained metal-–to–plastic total elbow replacement, author and date unknown.

Two pages of advertising literature, Souter Strathclyde™ Total Elbow System, Howmedica, date unknown.

Article entitled "Passive Motion of the Elbow Joint," Bernard F. Morrey, M.D. and Edmund Y.S. Chao, Ph. D., The Journal of Bone and Joint Surgery, vol. 58–A, No. 4, Jun. 1976, pp. 501–508.

* cited by examiner

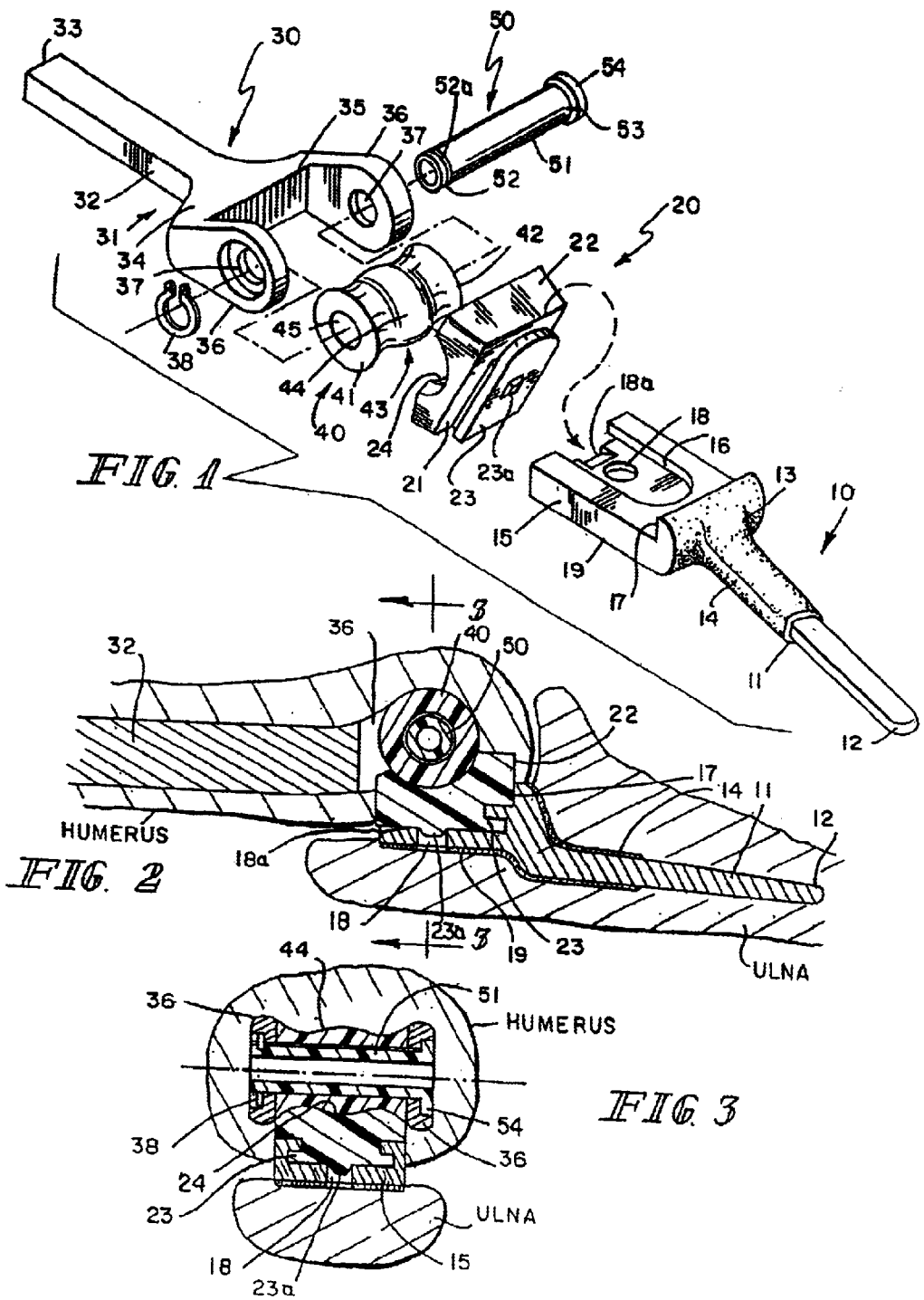

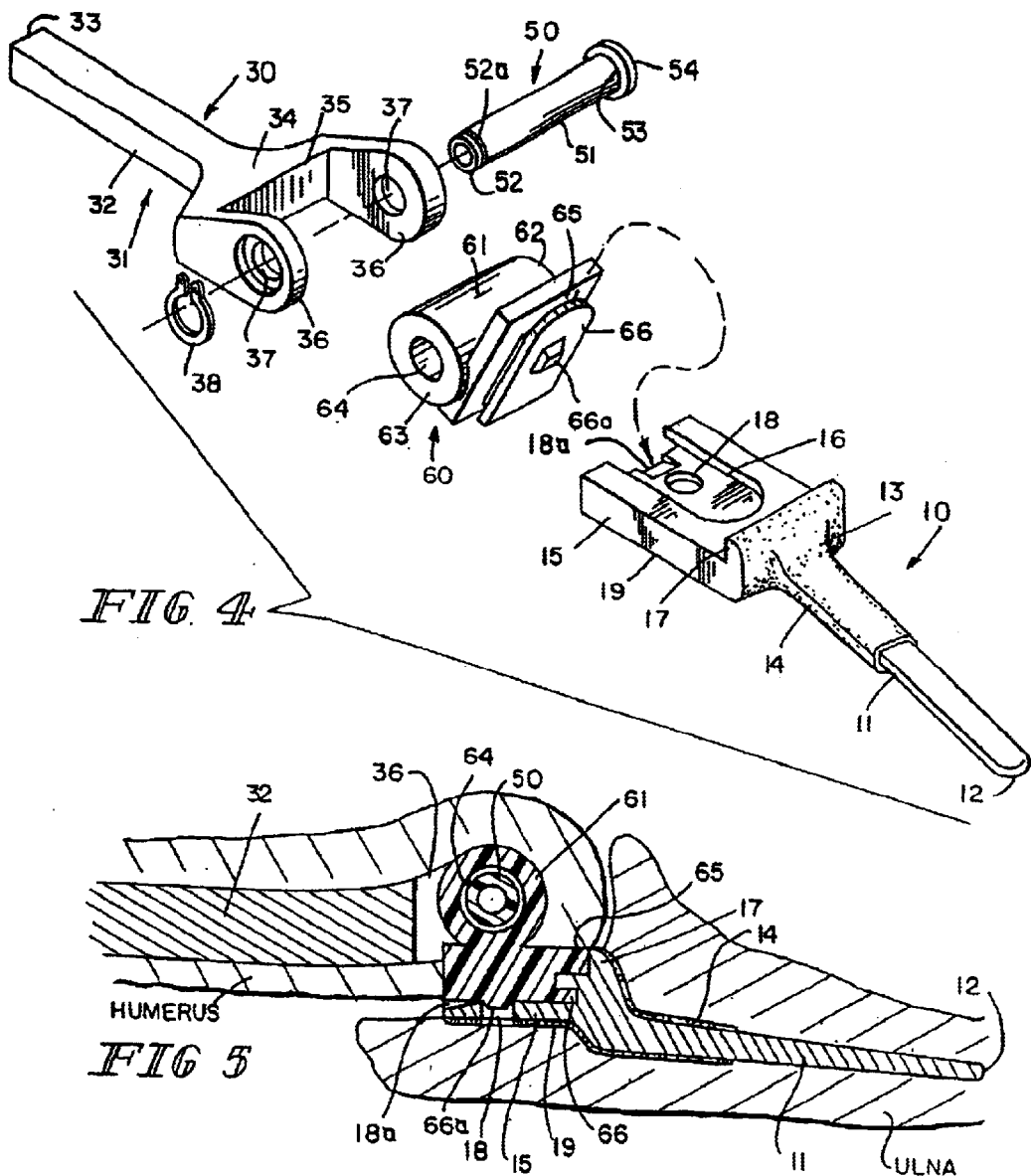

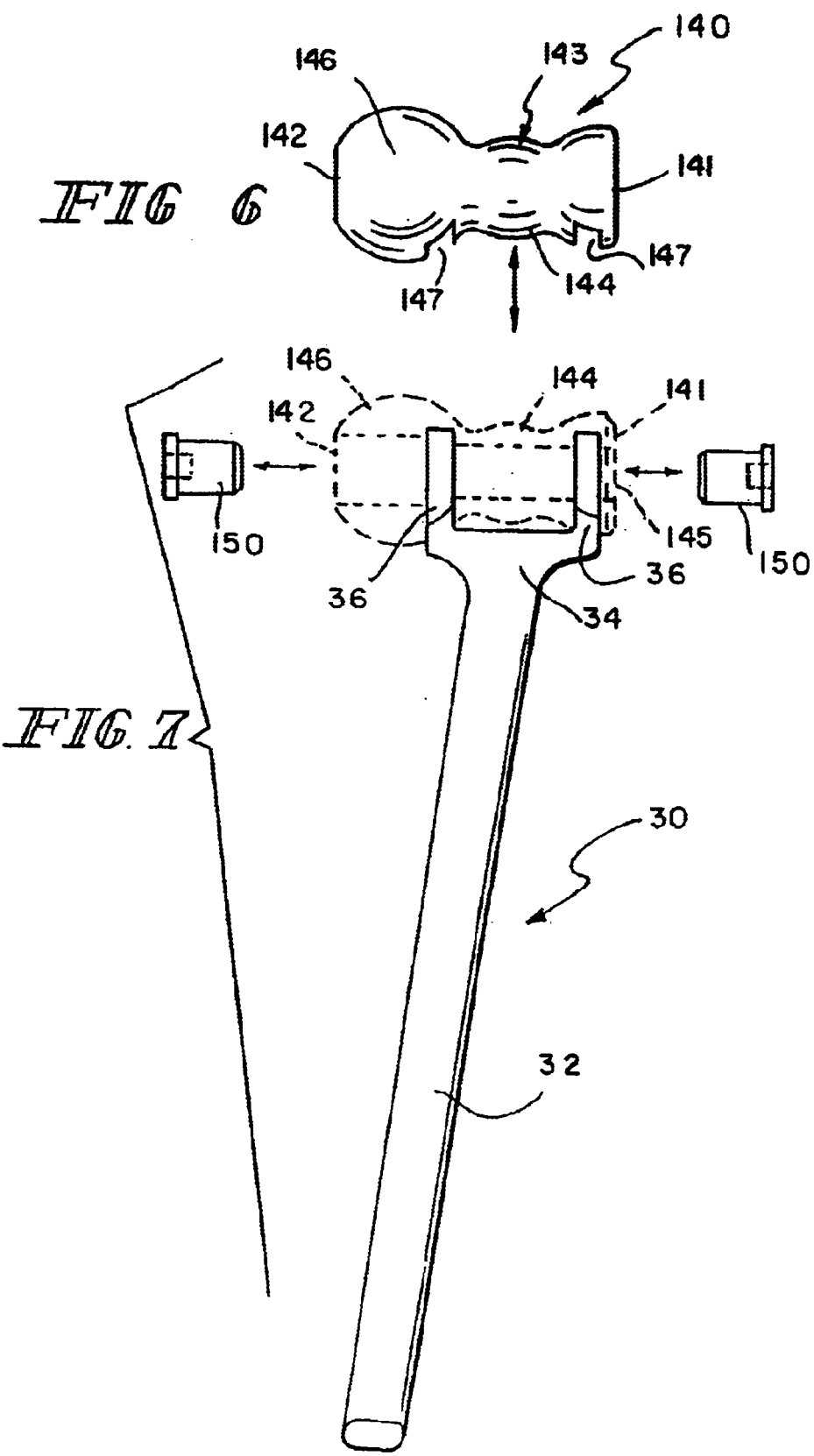

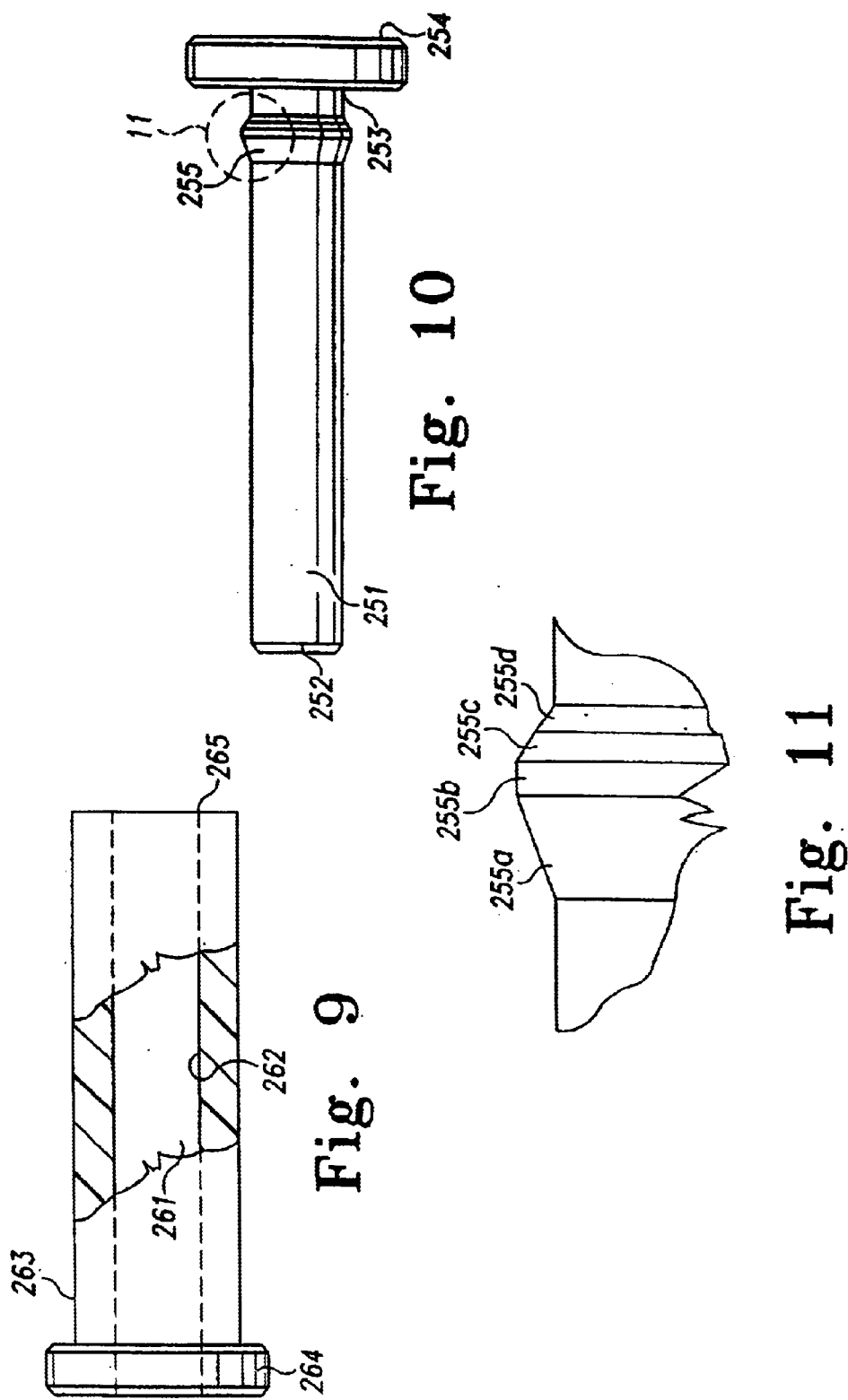

MODULAR ELBOW

This application is a continuation-in-part of U.S. patent application Ser. No. 09/222,601 filed Dec. 29, 1998, now U.S. Pat. No. 6,290,725 which is a continuation-in-part of U.S. patent application Ser. No. 08/963,138, filed Nov. 3, 1997 now U.S. Pat. No. 6,027,534.

BACKGROUND AND SUMMARY OF THE INVENTION

The present invention relates to artificial joints and, in particular, to a modular elbow prosthesis.

In the human elbow, three degrees of freedom are present. These are flexion-extension, varus-valgus (carrying angle) and axial rotation. Various elbow prostheses have been constructed as a replacement for the natural human elbow. The two basic types of elbow prosthesis known in the prior art are constrained and unconstrained. In constrained prosthesis, the prosthetic joint is held together mechanically, by components of the prosthesis. Such devices are shown, for example, in U.S. Pat. No. 5,376,121 to Huene et al., U.S. Pat. No. 3,708,805 to Scales, et al., U.S. Pat. No. 3,939,496 to Ling, et al., and U.S. Pat. No. 4,224, 695 to Grundei, et al. In an unconstrained device, the prosthetic device is held together by the patient's natural soft tissues. Such a device is shown in U.S. Pat. No. 4,293,963 to Gold, et al. In each of these devices, one portion of the prosthesis is implanted in the humerus of the patient and the other portion is implanted in the ulna. The two portions then mate in some manner to allow articulation of the joint. In the '695 patent to Grundei, et al., an additional portion of the prosthesis is implanted in the radius of the patient.

A surgeon may not always know prior to beginning an operation whether a patient would be better served by a constrained or unconstrained elbow prosthesis. Thus, it would be desirable to provide an elbow prosthesis that may be utilized in either the constrained or unconstrained manner.

It may also be necessary to convert an unconstrained elbow prosthesis to a constrained one, or vice versa, after implantation and use for a period of time. In order to do so, it is typically necessary to remove the portion of the prosthesis implanted in the humerus and ulna and to replace the entire prosthesis with either the constrained or unconstrained variety.

The present invention provides an elbow prosthesis that can be utilized in either a constrained or unconstrained fashion. The elbow prosthesis of the present invention can be converted from a constrained to an unconstrained prosthesis and from an unconstrained to a constrained prosthesis after implantation in a patient's body. Certain embodiments of the present invention also provide an elbow prosthesis that allows for three degrees of freedom: flexion-extension, varus-valgus (carrying angle) and axial rotation.

These features are attained by the provision of a modular prosthetic joint having a first stem, a second stem and three bearing components. The first stem has a first end and a second end and a body connected to it. A slot is formed in the body. The first bearing component has a flange configured to mate with the slot. A pair of arms extend from one end of the second stem. The second bearing component is adapted to fit between the arms of the second stem and configured to mate with the bearing surface of the first bearing component. The third bearing component is interchangeable with the first and second bearing components and is adapted to fit between the arms of the second stem. The third bearing component also includes a flange configured to mate with the slot.

According to one embodiment of the invention, the prosthesis includes an opening in each of the arms, an opening in the second bearing component and a pin adapted to extend through the openings in the arms and second bearing component.

In another embodiment, the prosthesis includes an opening in each of the arms, an opening in the third bearing component and a pin adapted to extend through the openings in the arms and the third bearing component.

In one embodiment of the invention, the bearing surface of the first bearing component is concave and the second bearing component includes a convex surface.

According to another embodiment of the invention, a modular prosthetic elbow includes an ulnar component having a stem with a first end adapted to fit within the medullary canal of a human ulna and a second end, a humeral component having a stem with a first end adapted to fit within the medullary canal of a human humerus, a first bearing component adapted to engage the ulnar component, a second bearing component adapted to engage the humeral component and mate with the first bearing component so as to be held in place by the soft tissues of the elbow, and a third bearing component interchangeable with the first and second bearing components, the third bearing component adapted to engage the ulnar component and be held in place by the humeral component.

In one embodiment, the ulnar component includes a slot and the first bearing component includes a flange configured to mate with the slot. The humeral component includes a pair of arms and the second bearing component is adapted to fit between the arms. An opening is formed in each of the arms and in the second bearing component and a pin is adapted to extend through the openings in the arms and the second bearing component.

In one embodiment, the humeral component includes a pair of arms and the third bearing component is adapted to fit between the arms. An opening is formed in each of the arms and in the third bearing component. A pin is adapted to extend through the openings in the arms and the third bearing component.

In another embodiment, a slot is formed in the ulnar component and a flange is connected to the third bearing component and configured to engage the slot. In another embodiment, a slot is formed in the ulnar component, a flange is connected to the first bearing component and configured to engage the slot, and another flange is formed on the third bearing component and configured to engage the slot.

In another embodiment of the invention, a prosthetic modular elbow includes an ulnar component having a proximal end and a distal end and a humeral component having a proximal end and a distal end. A first bearing mount is formed on the humeral component for engagement with at least two of a plurality of bearing components. A second bearing mount is located on the ulnar component for engagement with at least two of a plurality of bearing components. In one embodiment, the first bearing mount includes a pair of spaced apart arms extending from the humeral component. The arms may be located at the distal end of the humeral component. In another embodiment of the invention, the second bearing mount is located at the proximal end of the ulnar component and may include a slot formed in a portion of the ulnar component. In one embodiment of the invention, the first and second bearing mounts are configured to simultaneously engage one of the plurality of bearing components.

According to another embodiment of the present invention, a modular elbow prosthesis includes a humeral component with a bearing mount and an ulnar component with a bearing mount. First and second bearing components are configured to engage the humeral and ulnar bearing mounts respectively so as to form an unconstrained prosthesis. A third bearing component, interchangeable with the first and second bearing components, is configured to engage the humeral and ulnar components so as to form a constrained prosthetic elbow. The humeral bearing mount may include a pair of spaced apart arms. The ulnar bearing mount may include a slot. The third bearing component may include a cylindrical body with an opening therein and may have a flange attached thereto. The flange is configured to mate with the ulnar bearing mount. The first bearing component may include a flange configured to mate with the ulnar bearing mount. The second bearing component may include an opening.

In another embodiment of the present invention, a modular prosthetic elbow includes a humeral component, an ulnar component, a first bearing for joining the humeral and ulnar components to form a constrained prosthetic elbow and a set of bearings interchangeable with the first bearing for providing pivotal movement of the ulnar component relative to the humeral component in an unconstrained manner.

A method according to the present invention includes the steps of implanting a first component of a prosthesis in the ulna, implanting a second component of the prosthesis in the humerus and selecting from a group of three bearing components two bearing components, one to be joined to the first component of the prosthesis and a second to be joined to the second component of the prosthesis, or selecting the remaining bearing component and securing it to the first and second components of the prosthesis.

In one embodiment, the method further comprises the step of joining the first two bearing components to the first and second components so as to form an unconstrained prosthetic elbow. In another embodiment, the method further includes the step of joining the third bearing component to the first and second component so as to form a constrained prosthetic elbow.

In another embodiment of the invention, a prosthetic joint includes a first stem having a first end and a second end, a body connected to the first stem, a slot formed in the body, a first bearing component having a spherical bearing surface, a flange connected to the first bearing component and configured to mate with the slot, a second stem having a first end and a second end, a pair of arms extending from one end of the second stem and a second bearing component adapted to fit between the arms of the second stem and configured to mate with the bearing surface of the first bearing component. The second bearing component may include a spherical bearing surface. The prosthetic joint may include an opening in each of the arms, an opening in the second bearing component and a pin and sleeve adapted to extend through the openings in the arms and second bearing component. A ridge may be formed on a portion of the first stem and/or a portion of the body. A recessed area may be provided in the second bearing component for engaging at least one of the arms. An ear may be provided on the second stem. A nubbin may be located on the first bearing component and an opening may be provided in the body for engaging the nubbin.

In another embodiment of the invention, a prosthetic elbow includes an ulnar component having a stem with a first end adapted to fit within the medullary canal of an ulna and a second end, a first bearing component adapted to engage the ulnar component, a humeral component having a stem with a first end adapted to fit within the medullary canal of a humerus and a second bearing component having a spherical surface, the second bearing component being adapted to engage the, humeral component and mate with the first bearing component so as to be held in place by the soft tissues of the elbow.

In another embodiment of the invention, an elbow prosthesis includes a humeral component having a bearing mount, an ulnar component having a bearing mount and first and second bearing components, each including a spherical bearing surface, the first bearing component configured to engage the ulnar bearing mount and the second bearing component configured to engage the humeral bearing mount.

In another embodiment of the invention, a prosthetic elbow includes a humeral component, an ulnar component and a plurality of bearings for providing axial rotation of the ulnar component relative to the humeral component. At least one of the bearings may include a spherical bearing surface. The prosthetic elbow may provide a total of two or three degrees of freedom.

In another embodiment of the invention, an elbow prosthesis includes an ulnar component, a humeral component and means for providing axial rotation of the ulnar component with respect to the humeral component. The means for providing axial rotation may include a spherical bearing surface.

Another embodiment of the invention provides an elbow prosthesis including an ulnar component, a humeral component and means for providing at least three degrees of freedom between the ulnar and humeral components.

In another embodiment of the invention, a prosthetic elbow includes an ulnar component having a stem with a first end adapted to fit within the medullary canal of an ulna and a second end. A first bearing component is adapted to engage the ulnar component. A humeral component has a pair of arms and a stem with a first end adapted to fit within the medullary canal of a humerus. A second bearing component is adapted to engage the humeral component and mate with the first bearing component. The second bearing component has a pair of slots that engage the arms and form a taper lock therewith.

In yet another embodiment of the invention, an elbow prosthesis includes a humeral component having a bearing mount, an ulnar component having a bearing mount, and a bearing component configured to form a taper lock with the bearing mount on the ulnar component and to engage the bearing mount on the humeral component.

According to another embodiment of the invention, a modular elbow includes an ulnar component having a slot, a first bearing component having a flange configured to mate with the slot so as to form a taper lock, a humeral component having a pair of arms, and a second bearing component adapted to fit between the arms of the humeral component and configured to surround a portion of the first bearing component.

Other features of the present invention will become apparent from the following detailed description of the preferred embodiments and the accompanying drawings.

BRIEF DESCRIPTION OF THE DRAWINGS

FIG. 1 is an exploded perspective view of a modular elbow according to the present invention for use in the unconstrained configuration.

FIG. 2 is a longitudinal cross-sectional view showing the modular elbow of FIG. 1 implanted in the arm of a person.

FIG. 3 is a cross-sectional view taken along line 3—3 in FIG. 2.

FIG. 4 is an exploded perspective view of the modular elbow according to the present invention for use in the constrained mode.

FIG. 5 is a longitudinal cross-sectional view showing the modular elbow of FIG. 4 implanted in the arm of a person.

FIG. 6 is a plan view of an alternative second bearing component that forms a component of a modular elbow according to the present invention.

FIG. 7 is a plan view of the bearing component of FIG. 6 attached to a humeral component that is a component of modular elbow according to the present invention.

FIG. 9 is a partial cut-away, side elevational view of a sleeve that forms a component of the modular elbow shown in FIG. 8.

FIG. 10 is a side elevational view of a pin that forms a component of the modular elbow shown in FIG. 8.

FIG. 11 is a detail of the barb on the pin shown on FIG. 10.

DETAILED DESCRIPTION OF THE DRAWINGS

Figure 8:
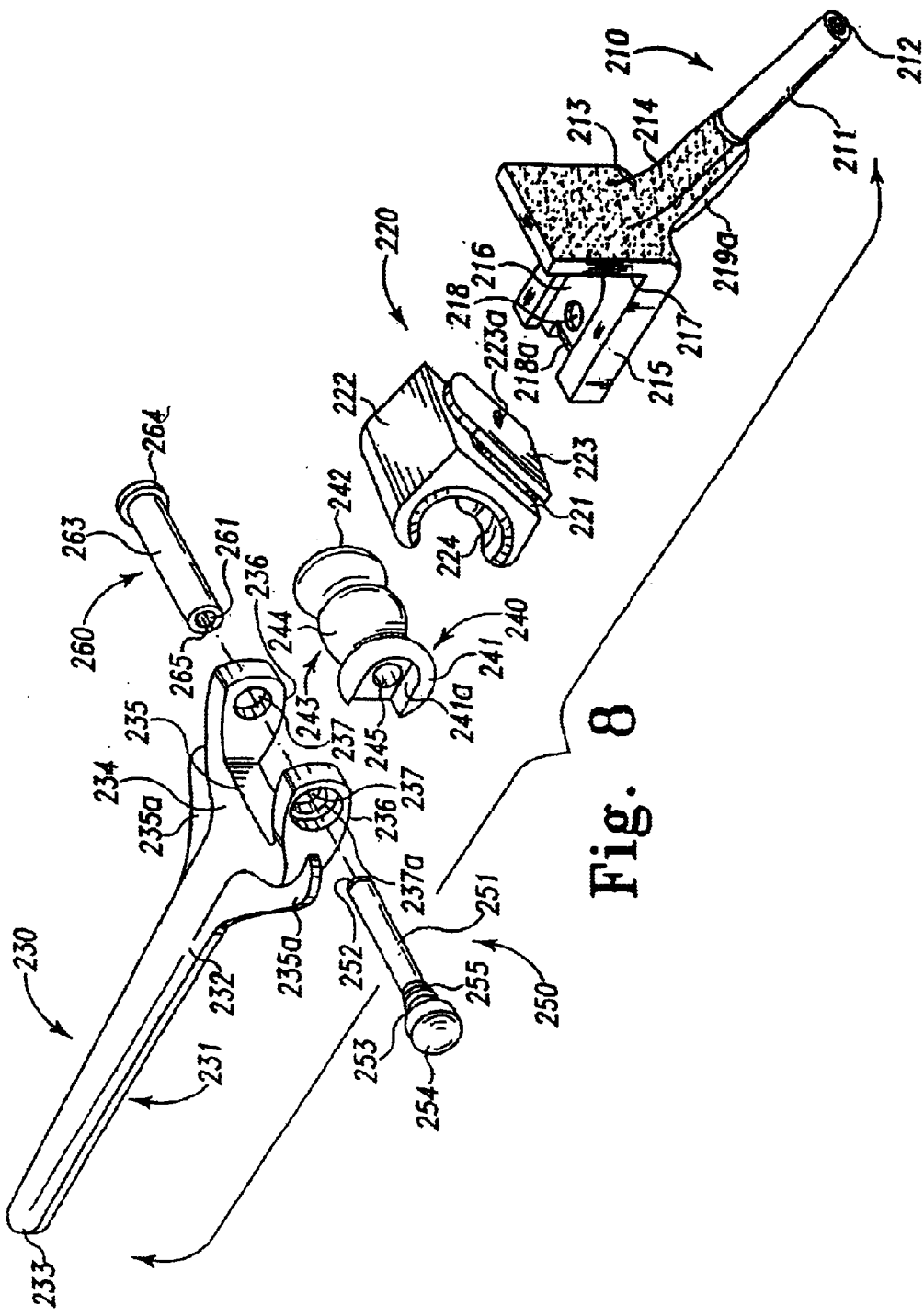
FIG. 8 is an-exploded view of another embodiment of a modular elbow according to the present invention for use in the unconstrained configuration.

FIG. 1 is an exploded perspective view of a modular elbow according to the present invention for use in the unconstrained mode. The modular elbow prosthesis comprises ulnar component 10, first bearing component 20, humeral component 30, second bearing component 40, and pin 50.

Ulnar component 10 comprises a stem 11 having a first or distal end 12 and a second or proximal end 13. A portion of stem 11 adjacent second end 13 may be coated with a material 14 to allow bone ingrowth between the stem and ulna. Any of various known bone ingrowth coatings, such as cobalt-chromium or titanium alloys, may be used. A generally rectangular body 15 is secured to second end 13 and has a slot 16 formed therein. Body 15 and slot 16 form a mount for a plurality of bearing components, as described below. Stem 11 extends from body 15 at an angle thereto. A raised stop member 17 is formed at the juncture of stem 11 and body 15. An opening 18 is formed in body 15 and is configured to receive a nubbin on first bearing component 20 or third bearing component 60, as described below. Body 15 further includes a sloped, recessed area or notch 18a utilized for guiding the nubbin into opening 18, as described below. Ulnar component 10 can be made from any surgical alloy, such as cobalt-chrome or titanium. Portions of ulnar component 10 other than or in addition to stem 11 may include a bone ingrowth coating. For example, bone ingrowth coating may be applied to underside 19 of body 15.

First bearing component 20 generally comprises a base 21 with a stop member 22 extending therefrom at a generally ninety degree angle. A flange 23 is formed on base 21 and is configured to mate with slot 16 in body 15 of ulnar component 10, as described below. A nubbin 23a extends from flange 23. Bearing component 20 further includes a concave bearing surface 24. Bearing surface 24 mates with second bearing component 40 as described below, when the modular elbow prosthesis is used in the unconstrained mode.

Humeral component 30 includes a stem 31 having a first segment 32 with a first or proximal end 33 and a second segment 34 with a second or distal end 35. Second segment 34 is integral with first segment 32 and widens with distance from first end 33. A pair of spaced apart arms 36 extend from second end 35 at an angle to second segment 34 of stem 31. Each arm 36 includes an opening 37. Arms 36 and openings 37 form a mount for a plurality of bearing components, as described below. A locking ring 38 is disposed about one opening 37. Humeral component 30 may also be made of a surgical alloy, such as cobalt-chrome.

Second bearing component 40 is a generally cylindrical member that flares outward at first end 41 and second end 42. Middle segment 43 of second bearing component 40 has a convex outer surface 44. The outer surface of second bearing component 40 mates with bearing surface 24 of first bearing component 20 when the modular elbow prosthesis is used in the unconstrained mode, as described below. Second bearing component 40 also includes a central opening or bore 45.

Pin 50 is a generally cylindrical member having a main body portion 51, a first end 52 and a second end 53. First end 52 includes a slot 52a to engage with locking ring 38 and secure pin 50 in place. Second end 53 includes an enlarged head or flange 54. Head 54 has a larger diameter than openings 37 in arms 36 of humeral component 30. A central opening or bore 55 extends through pin 50.

To use the elbow prosthesis of the present invention in the unconstrained mode (FIGS. 2 and 3), ulnar component 10 is implanted in an ulna such that stem 11 is located in the intramedullary canal as shown in FIG. 2. In a similar fashion, humeral component 30 is inserted in the humerus such that stem 31 is located in the intramedullary canal as shown in FIG. 2. Ulnar component 10 and humeral component 30 can be fixed to the ulna and humerus, respectively, with or without bone cement. First bearing component 20 is positioned such that flange 23 is adjacent slot 16 in body 15 of ulnar component 10. First bearing component 20 is then slid toward stop member 17. As this occurs, locking nubbin 23a engages notch 18a. As first bearing component 20 is moved into further engagement with ulnar component 10, locking nubbin 23a rides upward along notch 18a and is compressed by it. When first bearing component 20 is fully seated in ulnar component 10, locking nubbin 23a is located over opening 18 and decompresses. Locking nubbin 23a thus extends into opening 18a and prevents first bearing component 20 from pulling back out of slot 16 in body 15.

Second bearing component 40 is positioned between arms 36 of humeral component 30 such that opening 45 is aligned with opening 37. Pin 50 is then inserted through an opening 37 in one arm 36, through opening 45 in second bearing component 40 and through the remaining opening 37 in the other arm 36 such that locking ring 38 engages slot 52a. Second bearing component 40 is then placed adjacent first bearing component 20 such that their concave and convex surfaces mate. First and second bearing components 20 are held in position by the soft tissues of the elbow. In this manner, bearing components 20 and 40 articulate about their bearing surfaces and permit movement of the lower arm.

FIG. 4 shows an exploded perspective view of the components of the modular elbow prosthesis of the present invention for use in the constrained mode. In this mode, ulnar component 10, humeral component 30 and pin 50 of the unconstrained configuration are utilized in conjunction with a third bearing component 60. Third bearing component 60 includes a generally cylindrical member 61 having a first end 62, a second end 63 and a bore or opening 64 extending therethrough. Cylindrical member 61 is connected to base 65. A flange 66 is connected to base 65 opposite cylindrical body 61. Flange 66 is configured to mate with slot 16 of body 15 in the same way as previously described for first bearing component 20. A locking nubbin 66a is formed on flange 66. First bearing component 20, second bearing component 40 and third bearing component 60 may all be made from surgical metal or plastic, such as ultra-high molecular weight polyethylene.

To implant the modular elbow of the present invention in the constrained mode, ulnar component 10 is implanted in the ulna such that stem 11 is located in the intramedullary canal as shown in FIG. 5. Similarly, stem 31 of humeral component 30 is positioned in the intramedullary canal of the humerus as shown. Third bearing component 60 is then secured to body 15 of ulnar component 10 by sliding flange 66 in groove 16 of body 15 until locking nubbin 66a engages opening 18. Cylindrical body 61 of third bearing component 60 is then positioned between arms 36 of humeral component 30 such that opening 64 is aligned with openings 37 in arms 36. Pin 50 is then inserted through one opening 37 in an arm 36, through opening 64 in third bearing component 60 and through opening 37 in the remaining arm 36 such that locking ring 38 engages slot 52a. In this manner, third bearing component 60 can articulate about pin 50 between arms 36. Third bearing component 60 is held in place by pin 50 and arms 36, rather than the soft tissues of the elbow.

Thus, with the present invention, a modular prosthesis kit is provided that allows for intra-operative implantation of a constrained or unconstrained elbow prosthesis. Additionally, if it is necessary to convert an unconstrained prosthesis to a constrained configuration, with the present invention, the change can be made after implantation and without removing the ulnar and humeral components. To do so, the arm is surgically opened and pin 50 and second bearing component 40 are removed from arms 36 on the humeral component. First bearing component 20 is removed from ulnar component 10 by compressing locking nubbin 23a and sliding flange 23 out of slot 16. Third bearing component 60 is then secured to ulnar component 10 by inserting flange 66 into slot 16. Cylindrical body 61 is then positioned between arms 36 such that opening 64 is aligned with openings 37 in arms 36. A pin 50 is then inserted through the openings in arms 36 and third bearing component 60 and locked in place with lock ring 38. In this manner, a surgeon is provided with a modular elbow prosthesis kit that allows the surgeon to decide, after surgery has begun, whether to utilize a constrained or unconstrained prosthesis. Furthermore, the present invention provides a prosthesis that can be converted from a constrained to an unconstrained configuration, or vice versa, without removing the ulnar and humeral components from the patient.

FIGS. 6 and 7 show an alternative embodiment of the second bearing component attached to humeral component 30. Second bearing component 140 includes a generally cylindrical member having a first and 141 and a second and 142. The middle segment 143 of second bearing component 140 includes a convex outer surface 144. The outer surface of second bearing component 140 mates with bearing surface 24 of first bearing component 20 when the modular elbow prosthesis is used in the unconstrained mode. Bearing component 140 also includes a central opening or bore 145 extending therethrough. Adjacent second end 142 is an enlarged body or head 146. A pair of slots or openings 147 are formed in bearing component 140.

To secure bearing component 140 to humeral component 30, arms 36 are inserted into slots 147 such that openings 37 therein align with opening or bore 145 in bearing component 140. Openings 37 may be threaded to receive screws 150 to secure bearing component 140 to humeral component 30. Alternatively, a pin and locking ring arrangement, as described above, may be used. Additional methods of securing bearing component 140 to humeral component 30 may also be used.

FIG. 8 is an exploded perspective view of another embodiment of a modular elbow according to the present invention for use in the unconstrained mode. The modular elbow prosthesis comprises ulnar component 210, first bearing component 220, humeral component 230, second bearing component 240, pin 250 and sleeve 260.

Ulnar component 210 comprises a stem 211 having a first or distal end 212 and a second or proximal end 213. A portion of stem 211 adjacent second end 213 may be coated with a material 214 to allow bone ingrowth between the stem and ulna. Any of various known bone ingrowth coatings, such as cobalt-chromium or titanium alloys, may be used. A generally rectangular body 215 is secured to second end 213 and has a slot 216 formed therein. Body 215 and slot 216 form a mount for at least one bearing component, as described below. Stem 211 extends from body 215 at an angle thereto. A raised stop member 217 is formed at the juncture of stem 211 and body 215. An opening 218 is formed in body 215 and is configured to receive a nubbin on first bearing component 220, as described below. Body 215 further includes a sloped, recessed area or notch 218a utilized for guiding the nubbin into opening 218, as described below. Ulnar component 210 also includes a ridge 219a on underside 219 of body 215 and stem 211. Ridge 219a helps stabilize ulnar component 210 in the intermedullary canal of the ulna by preventing rotation. Ulnar component 210 can be made from any surgical alloy, such as cobalt-chrome or titanium. Portions of ulnar component 210 other than or in addition to stem 211 may include a bone ingrowth coating. For example, bone ingrowth coating may be applied to underside 219 of body 215.

First bearing component 220 generally comprises a base 221 with a stop member 222 extending therefrom at a generally ninety degree angle. A flange 223 is formed on base 221 and is configured to mate with slot 216 in body 215 of ulnar component 210, as described below. A nubbin 223a extends from flange 223. Bearing component 220 further includes a concave, spherical bearing surface 224. Bearing surface 224 mates with second bearing component 240 as described below, when the modular elbow prosthesis is used in the unconstrained mode.

Humeral component 230 includes a stem 231 having a first segment 232 with a first or proximal end 233 and a second segment 234 with a second or distal end 235. Second segment 234 is integral with first segment 232 and widens with distance from first end 233. A pair of ears 235a is provided adjacent distal end 235 of humeral component 230. Ears 235a help to stabilize humeral component 230 in the intermedullary canal of the humerus by preventing rotation. A pair of spaced apart arms 236 extend from second end 235 at an angle to second segment 234 of stem 231. Each arm 236 includes an opening 237. Note that in the embodiment shown, arms 236 are keyed about openings 237 by providing a recessed area 237a. Arms 236 and openings 237 form a mount for at least one bearing component, as described below. Humeral component 230 may also be made of a surgical alloy, such as cobalt-chrome.

Second bearing component 240 includes a first end 241, a second end 242 and a middle segment 243. Ends 241 and 242 are keyed with recessed areas 241a and 242a generally corresponding in shape to arms 236. This prevents second bearing component 240 from rotating with respect to arms 236. Middle segment 243 of second bearing component 240 has a convex, spherical bearing surface 244. Bearing surface 244 of second bearing component 240 mates with bearing surface 224 of first bearing component 220 when the modular elbow prosthesis is used in the unconstrained mode, as described below. Second bearing component 240 also includes a central opening or bore 245.

Pin 250 is a generally cylindrical member having a main body portion 251, a first end 252 and a second end. Second end 253 includes an enlarged head or flange 254. Head 254 has a larger diameter than openings 237 in arms 236 of humeral component 230 and is shaped to generally correspond to the shape of areas 237a. A barb 255 is located on body portion 251. Barb 255 includes a first, angled segment 255a, a second segment 255b generally parallel to body portion 251, a third, angled segment 255c and a fourth, angled segment 255d. Barb 255 secures pin 250 to sleeve 260 as described below. Pin 250 is preferably made from a metal material. However, other materials can also be utilized.

Sleeve 260 is a generally cylindrical member having a bore 261, an interior wall 262, an exterior wall 263, an enlarged head 264 and an edge 265. Head 264 has a larger diameter than openings 237 in arms 236 of humeral component 230 and is shaped to generally correspond to the shape of areas 237a. Bore 261 is roughly the diameter of body portion 251 and is smaller in diameter than second segment 255b. Sleeve 260 is preferably made from ultra high molecular weight polyethylene. However, other materials can also be utilized.

To use the elbow prosthesis of the present invention in the unconstrained mode, ulnar component 210 is implanted in an ulna such that stem 211 is located in the intramullary canal. In a similar fashion, humeral component 230 is inserted in the humerus such that stem 231 is located in the intramedullary canal. Ulnar component 210 and humeral component 230 can be fixed to the ulna and humerus, respectively, with or without bone cement. First bearing component 220 is positioned such that flange 223 is adjacent slot 216 in body 215 of ulnar component 210. First bearing component 220 is then slid toward stop member 217. As this occurs, locking nubbin 223a engages notch 218a. As first bearing component 220 is moved into further engagement with ulnar component 210, locking nubbin 223a rides upward along notch 218a and is compressed by it. When first bearing component 220 is fully seated in ulnar component 210, locking nubbin 223a is located over opening 218a and decompresses. Locking nubbin 223a thus extends into opening 218a and prevents first bearing component 220 from pulling back out of slot 216 in body 215. Second bearing component 240 is positioned between arms 236 of humeral component 230 such that opening 245 is aligned with opening 237 and arms 236 extend into recessed areas 241a and 242a.

Sleeve 260 is then inserted through an opening 237 in one arm 236, through opening 245 in second bearing component 240 until head 264 is located in recessed area 237a. Pin 250 is then inserted through opening 237 in the other arm 236 and into bore 261 of sleeve until head 254 is located in recessed area 237a. As pin 250 is inserted into bore 261, edge 265 rides along first segment 255a and expands or deforms bore 261 so that barb 255 can be fully located within bore 261. If an attempt is made to-remove pin 250 from sleeve 260, barb 250 will cut into or otherwise engage interior wall 262, thereby resisting removal.

Second bearing component 240 is then placed adjacent first bearing component 220 such that their concave and convex surfaces mate. First and second bearing components 220 are held in position by the soft tissues of the elbow. In this manner, bearing components 220 and 240 articulate about their bearing surfaces and permit movement of the lower arm.

Figure 12:
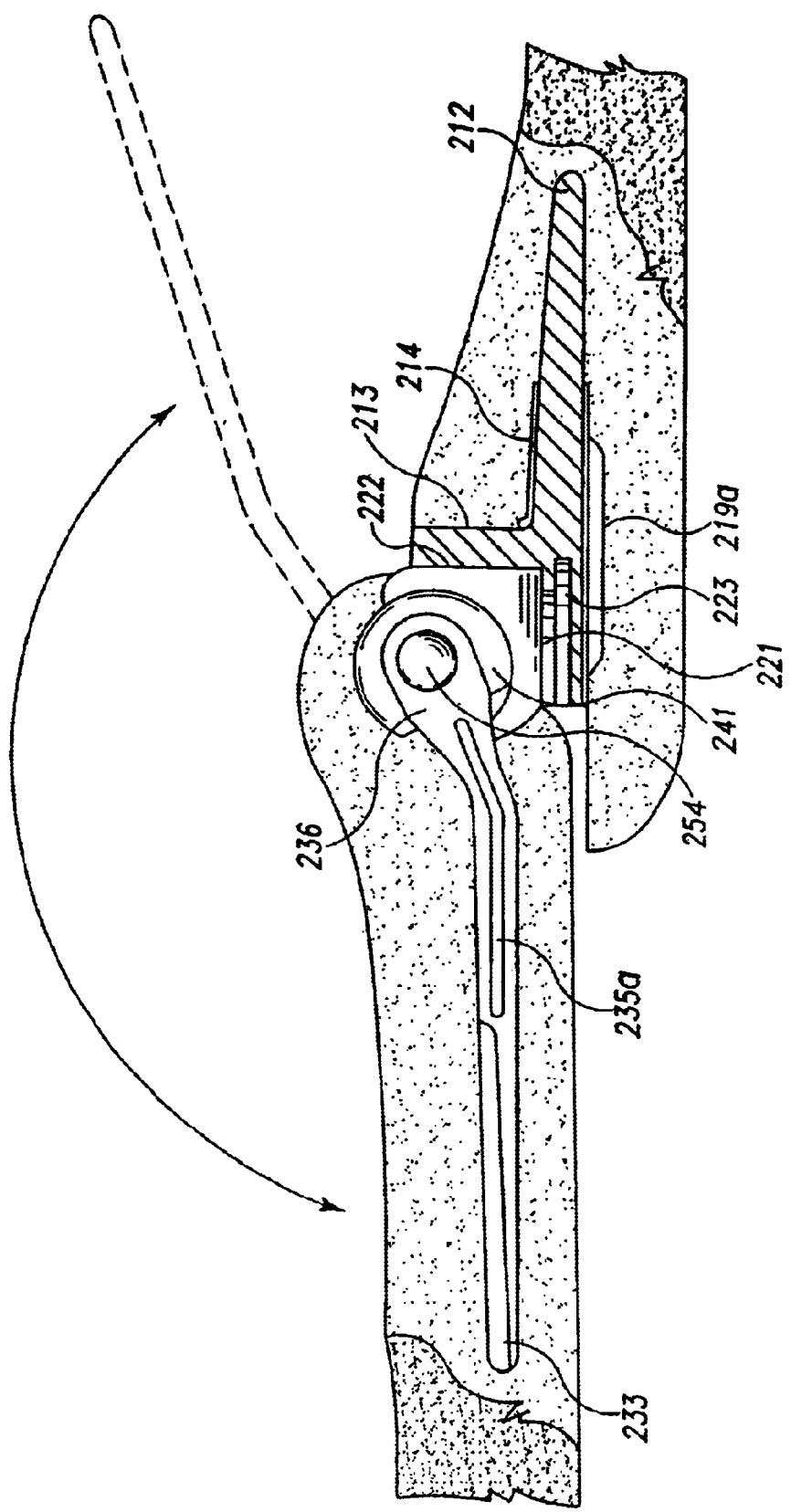
FIG. 12 shows the modular elbow of FIG. 8 implanted in a patient and illustrates one degree of freedom of motion permitted by the elbow.

As shown in FIG. 12, bearing components 220 and 240 articulate to permit movement similar to the flexion-extension type, thus providing a first degree of freedom of motion.

Figure 13:
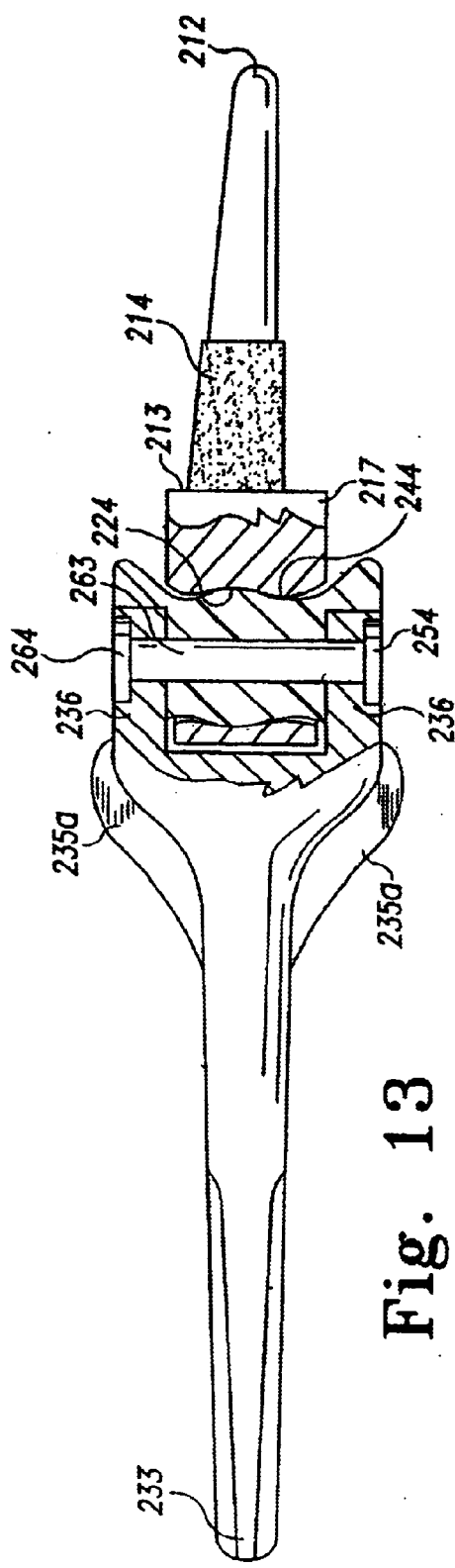
FIG. 13 is a partial cut-away view showing the modular elbow of FIG. 8 in a neutral position.
Figure 14:
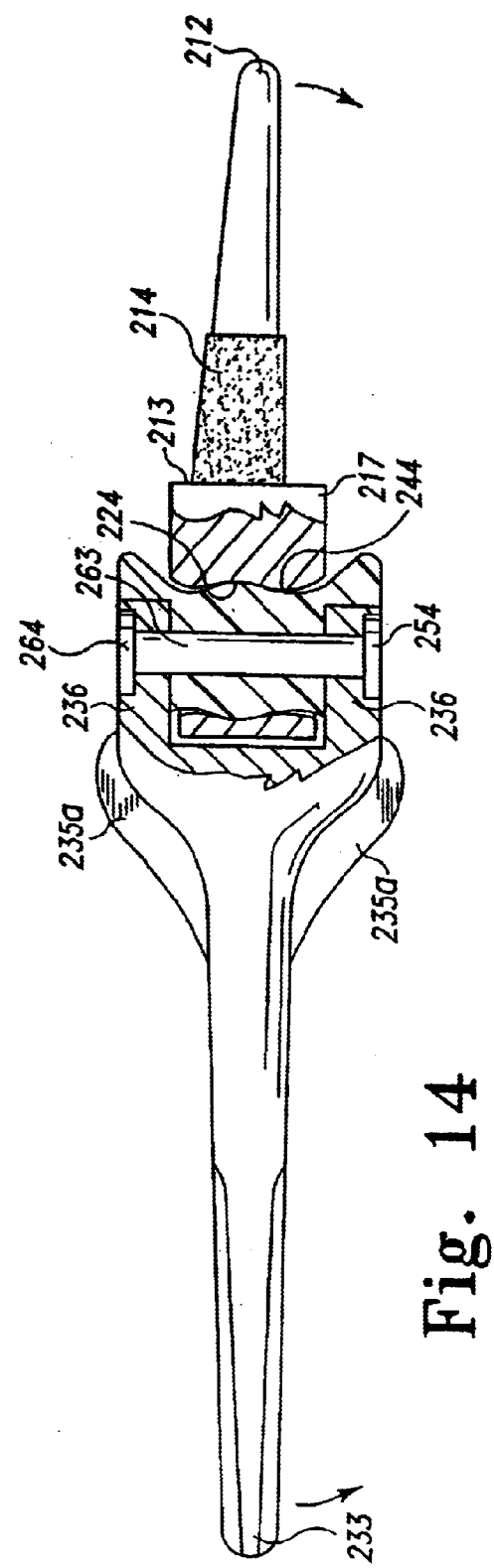
FIG. 14 is a partial cut-away view illustrating a second degree of freedom of motion permitted by the modular elbow of FIG. 8.

As shown in FIGS. 13 and 14, this embodiment of the invention also permits lateral movement between the bearing components. FIG. 13 shows the elbow in a neutral position, i.e., bearing component 220 is centered with respect to bearing component 240. FIG. 14 illustrates the position of bearings 220 and 240 when the prosthesis moves as indicated by the arrows in FIG. 14. As can be seen, bearing components 220 and 240 shift with respect to one another while still maintaining contact. Thus, the prosthesis presents a second degree of freedom of motion.

Figure 15:
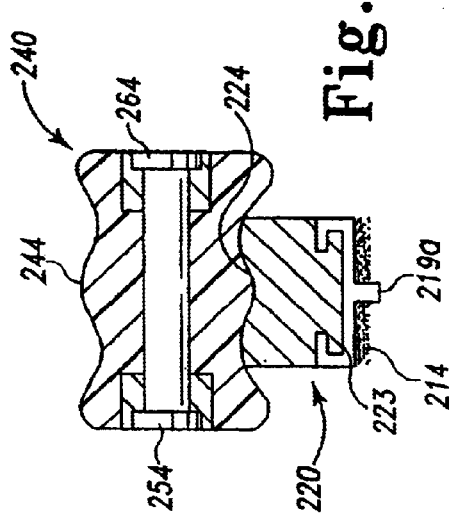
FIGS. 15–17 are partial cut-away views illustrating the manner in which the modular elbow of FIG. 8 permits a third degree of freedom of motion.
Figure 17:
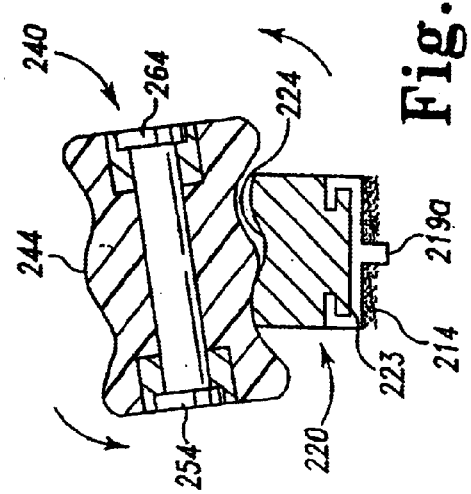
Figure 16:
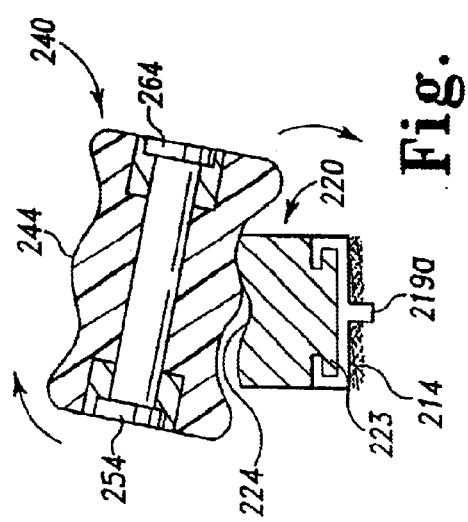

Additionally, bearing components 220 and 240 permit axial rotation, as shown in FIGS. 15 through 17, thereby providing a third degree of freedom of motion. FIG. 15 shows the relative position of bearing components 220 and 240 in the neutral position. FIGS. 16 and 17 indicate that as the joint is subject to axial rotation, as indicated by the arrows, the bearing components 220 and 240 shift as indicated. However, because bearing surfaces 224 and 244 are spherical, they maintain contact even during axial rotation.

As with the embodiment of FIGS. 1–5, the embodiment of FIG. 8 could also be converted for use in the constrained mode. To do so, bearing components 220 and 240 would be removed and replaced with a bearing component similar to third bearing component 60.

Figure 18:
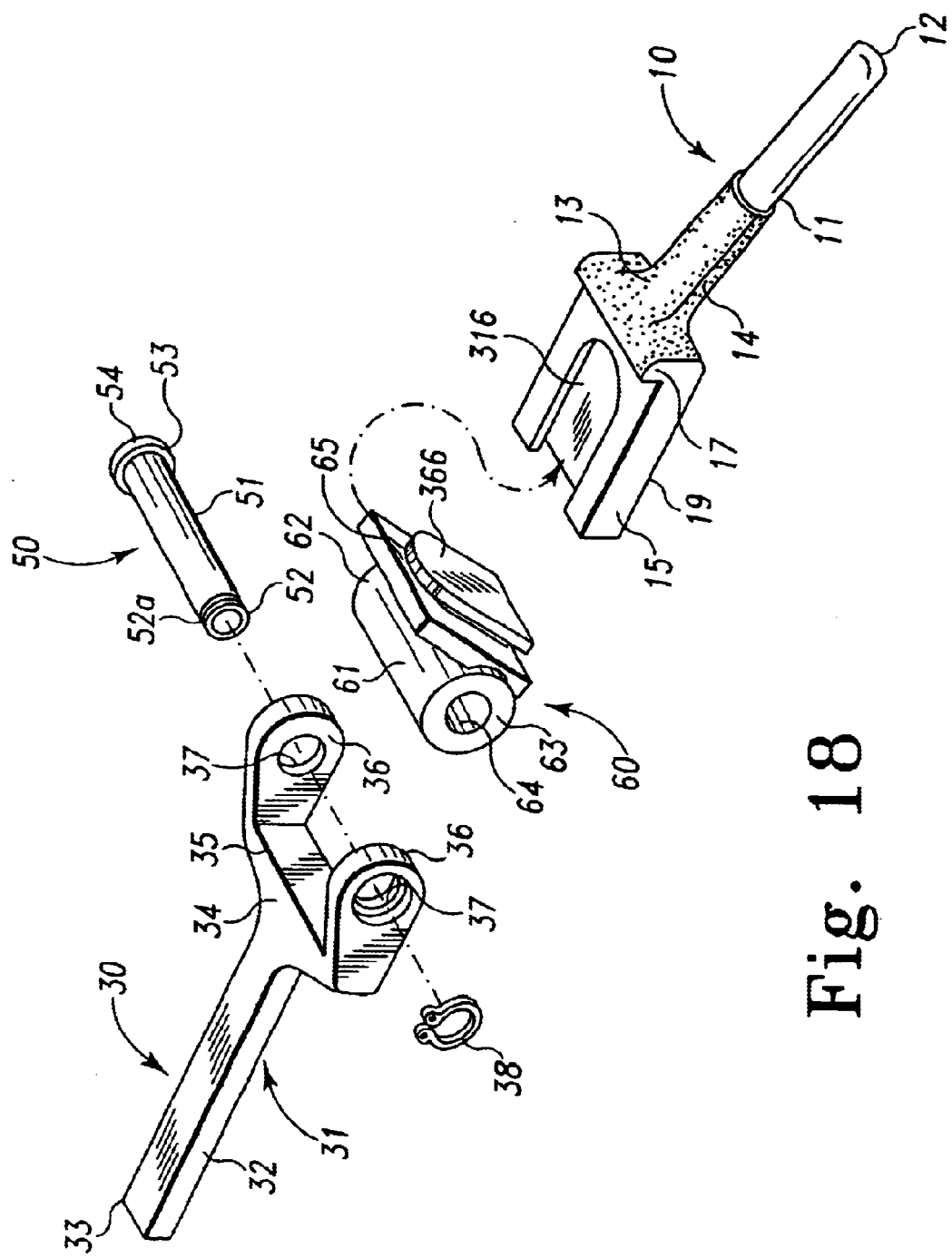
FIG. 18 is an exploded view of another embodiment of a modular elbow according to the present invention for use in the constrained configuration.

FIG. 18 shows another embodiment of a modular elbow according to the present invention for use in the constrained configuration. In this embodiment, nubbin 66a has been removed from flange 66 on bearing component 60. Notch 18a and opening 18 have been eliminated from ulnar component 10. In this embodiment, flange 366 and slot 316 are configured so as to form a taper lock, commonly referred to as a Morse taper. The taper lock configuration is self-locking and designed to reduce micro motion between flange 366 and slot 316. While the taper lock configuration may include any one of a variety of acceptable taper angles, an angle of less than ten degrees is preferred. Thus, when flange 366 is fully seated within slot 316, bearing component 60 is secured to ulnar component 10.

Figure 19:
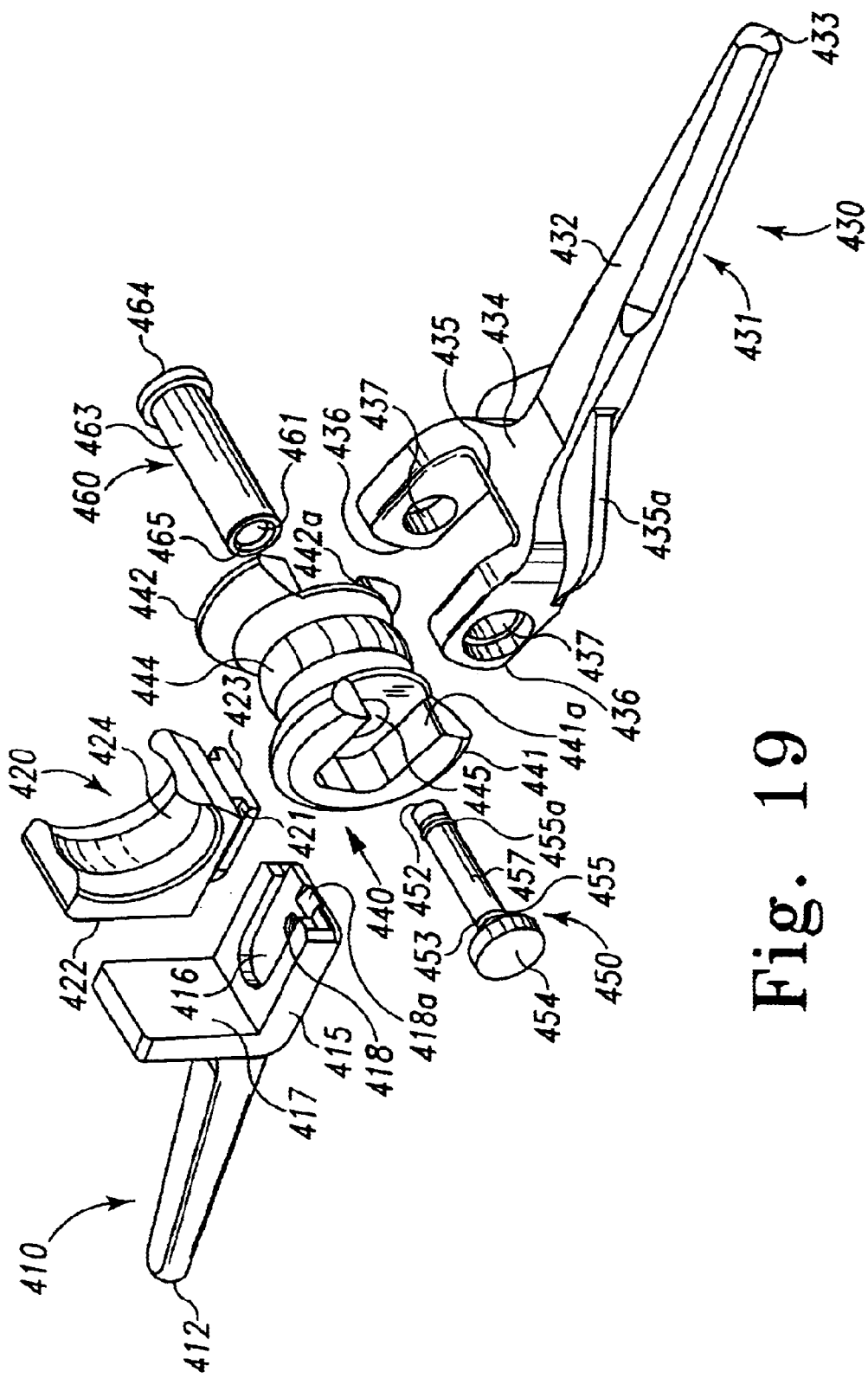
FIG. 19 is an exploded view of another embodiment of a modular elbow according to the present invention for use in an unconstrained configuration.

FIG. 19 shows yet another embodiment of a prosthetic elbow for use in the unconstrained configuration. This embodiment is similar to that shown in FIG. 8. In FIG. 19, a numeral "4" has been substituted at the beginning of the reference numbers for the numeral "2" to show corresponding elements with FIG. 8. In this embodiment, arms 436 of humeral component 430 engage recessed areas 441a and 442a and form a taper lock therewith similar to the taper lock described above. Thus, by fully engaging arms 436 and recessed areas or slots 441a and 442a, bearing component 44b is secured to humeral component 430. Note that this embodiment also utilizes a pin 450 and a sleeve 460 to further secure bearing component 440 to humeral component 430. The use of pin 450 and sleeve 460 provides a redundant locking function in the event recessed areas 441a disengage from arms 436. Note also that in this embodiment, pin 450 has been provided with an additional barb 455a for securing pin 450 within sleeve 460. Note also that notch 418a and opening 418 in ulnar component 410 and nubbin 466a (not shown) could be eliminated from bearing component 420 as shown in the embodiment of FIG. 18. If this is done, flange 423 and slot 416 in ulnar component 410 would be configured so as to form a taper lock to secure those components in a manner similar to that described above.

Figure 20:
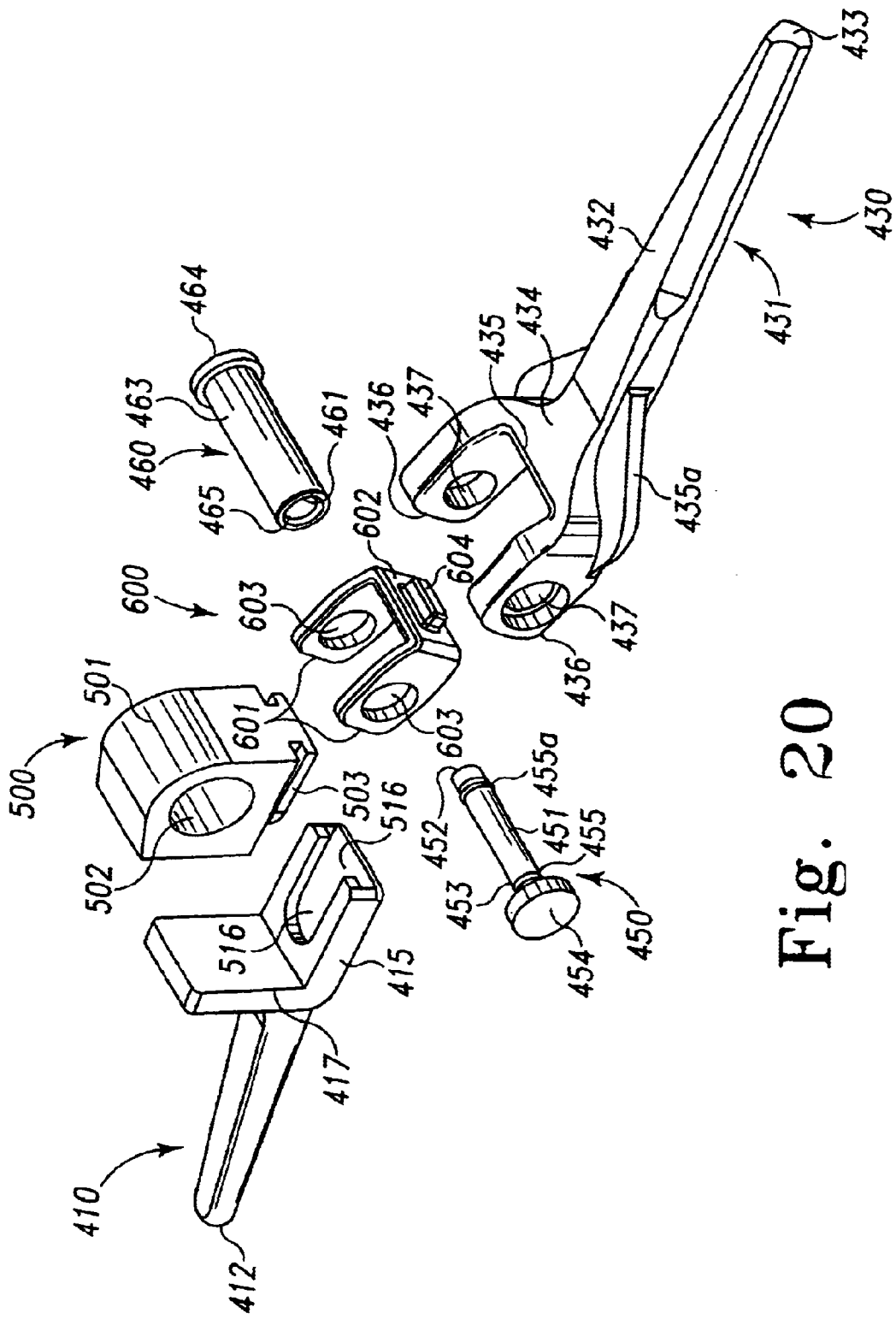
FIG. 20 is an exploded view of another embodiment of a modular elbow according to the present invention for use in the constrained configuration.

FIG. 20 shows yet another embodiment of a modular elbow for use in the constrained configuration. This embodiment is similar to that shown in FIG. 19 and corresponding numbers indicate corresponding parts. In this embodiment, bearing 420 and bearing 440 have been replaced by bearings 500 and 600. Bearing 500 includes a body 501 having an opening 502 extending therethrough. A flange 503 is formed on the bottom of body 501. Ulnar component 410 had been modified to remove opening 418 and notch 418a. Slot 516 in ulnar component 410 and flange 503 on bearing component 500 are configured to form a taper lock similar to the taper lock formed between flange 366 and slot 316 (FIG. 18). Thus, fully inserting flange 503 in slot 516 secures bearing 500 to ulnar component 410.

Bearing 600 includes a pair of arms 601 extending from a base 602. A pair of openings 603 extend through arms 601. Bearing component 600 is configured and sized such that it can fit between arms 436 of humeral component 430. A projection 604 is formed on base 602 of bearing component 600. Projection 604 engages a corresponding slot or opening (not shown) in second end 35 of humeral component 410 so as to stabilize bearing component 600 between arms 436. Projection 604 and the opening in second end 435 of humeral component 430 can be configured to form a taper lock to assist in securing bearing component 600 to humeral component 430.

In use, bearing component 600 is positioned between arms 436 such that openings 603 align with openings 437. Bearing component 500 is secured to ulnar component 410 through the taper lock connection of flange 503 in slot 516. Arms 601 of bearing component 600 are then positioned about body 501 such that opening 603s are aligned with opening 502. Pin 450 and sleeve 460 are then used to secure bearing component 600 and bearing component 500 in place.

Although the present invention has been shown and described in detail the same is to be taken by way of example only and not by way of limitation. Numerous changes can be made to the embodiments shown without departing from the scope of the, invention. For example, the shapes of the various component can be changed, so long as the principals of the operation are maintained. Also, either the pin and locking ring arrangement of FIG. 1 or the pin and sleeve arrangement of FIG. 8 can be used with either set of ulnar and humeral components and bearings. Accordingly, the invention is to be limited only by the terms of the claims appended hereto.

What is claimed is:

1. A prosthetic elbow, comprising: an ulnar component having a stem configured to be received within the medullary canal of an ulna;

a first bearing component coupled to said ulnar component;

a humeral component having a first arm and a second arm spaced apart from each other to define a bearing space, said humeral component further having a humeral stem configured to be received within the medullary canal of a humerus; and a second bearing component configured to be received within said bearing space and mate with said first bearing component, wherein said second bearing component has (i) a first lateral bearing end portion having a first lateral recessed area defined therein, and (ii) a second lateral bearing end portion having a second lateral recessed area defined therein, wherein said first arm is configured to be received in said first lateral recessed area so as to form a first taper lock connection between humeral component and said second bearing component, and wherein said second arm is configured to be received in said second lateral recessed area so as to form a second taper lock connection between humeral component and said second bearing component.

2. The prosthetic elbow of claim 1, further comprising a pin, wherein:

said second bearing component has a bearing opening extending therethough, said first arm has a first arm opening extending therethough, said second arm has a second arm opening extending therethough, and said pin extends through said bearing opening, said first arm opening and said second arm opening.

3. The prosthetic elbow of claim 2, further comprising a sleeve, wherein:

said sleeve extends through said bearing opening, said first arm opening and said second arm opening, and said pin is positioned in a central passage of said sleeve.

4. The prosthetic elbow of claim 3, wherein said pin is configured to be secured within said sleeve.

5. The prosthetic elbow of claim 1, wherein both said first taper lock connection and said second taper lock connection includes a taper angle of less than ten degrees.

6. The prosthetic elbow of claim 1, wherein:

said first bearing component includes a concave bearing surface portion, said second bearing component includes a convex bearing surface portion, and said concave bearing surface portion is configured to mate with said convex bearing surface portion.

7. A prosthetic assembly, comprising:

a prosthetic bone component having a first arm and a second arm spaced apart from each other to define a bearing space therebetween, said prosthetic bone component further having a stem configured to be received within the medullary canal of a natural bone; and a bearing component configured to be positioned within said bearing space, wherein said bearing component has (i) a first lateral bearing end portion having a first lateral recessed area defined therein, and (ii) a second lateral bearing end portion having a second lateral recessed area defined therein, wherein said first arm is configured to be received in said first lateral recessed area so as to form a first taper lock connection between prosthetic bone component and said bearing component, and wherein said second arm is configured to be received in said second lateral recessed area so as to form a second taper lock connection between prosthetic bone component and said bearing component.

8. The prosthetic assembly of claim 7, wherein said stem is further configured to be received within the medullary canal of a humerus.

9. The prosthetic elbow of claim 7, further comprising a pin, wherein:

said bearing component has a bearing opening extending therethough, said first arm has a first arm opening extending therethough, said second arm has a second arm opening extending therethough, and said pin extends through said bearing opening, said first arm opening and said second arm opening.

10. The prosthetic elbow of claim 9, further comprising a sleeve, wherein:

said sleeve extends through said bearing opening, said first arm opening and said second arm opening, and said pin is positioned in a central passage of said sleeve.

11. The prosthetic elbow of claim 10, wherein said pin is configured to be secured within said sleeve.

12. The prosthetic elbow of claim 7, wherein both said first taper lock connection and said second taper lock connection includes a taper angle of less than ten degrees.

13. The prosthetic elbow of claim 7, wherein said bearing component includes a convex bearing surface portion configured to mate with a concave bearing surface portion of another bearing component.

* * * * *